US00PP13752P29

(12) United States Plant Patent
Zwetzig et al.

(10) Patent No.: US PP13,752 P2
(45) Date of Patent: Apr. 29, 2003

(54) HIBISCUS PLANT NAMED 'ERUPTION'

(76) Inventors: Gretchen Angela Zwetzig, 8101 S. 14th St., Lincoln, NE (US) 68512; David Whitman Fleming, deceased, late of Lincoln, NE (US), by Gretchen Zwetzig, legal representative ( * ) Notice: Subject to any disclaimer, the term of this patent is extended or adjusted under 35 U.S.C. 154(b) by 0 days.

(21) Appl. No.: 10/207,250

(22) Filed: Jul. 30, 2002

(51) Int. Cl.[7] ..... A01H 5/00
(52) U.S. Cl. ..... Plt./257

(58) Field of Search ..... Plt./257

*Primary Examiner*—Bruce R. Campell
*Assistant Examiner*—W C Haas

(57) ABSTRACT

A new and distinct cultivar of winter hardy hibiscus plant named 'Eruption' is the result of a unique hybridization. This new and distinct cultivar is characterized primarily as to novelty by, its extreme cold hardiness to Zone 4, large, thick-textured, reddish-purple flowers and its green "oak-leaved" appearance cast with a purple cast compactness of about 3 feet, its vigorous and uniform growth habit, and its floriferous nature from midsummer until frost.

1 Drawing Sheet

BOTANICAL CLASSIFICATION

*Hibiscus moscheutos×H. coccineus.*

BACKGROUND OF THE NEW PLANT

The new plant of this invention is the result of a unique hybridization, with the breeding achievement being evidenced in the outstanding combination of characteristics exhibited by this new and distinct Hibiscus plant, which include:

(a) Refined 3–5 lobed "Oak to Maple shaped" green leaves with a purple cast and relatively smooth margins which combined compliments the landscape;
(b) Medium-sized flowers that are outstanding for their bright fuscia colored, thick textured petals;
(c) The plant being very floriferous with flowers that stay open at least one full day;
(d) The plant being medium-sized but vigorous with compact and uniform breaking action which gives it unique landscape utility; and
(e) The plant being so hardy that it can consistently withstand winter temperatures of at least −30 degrees Fahrenheit.

SUMMARY OF THE INVENTION

'Eruption' was the result of a 40-year breeding program. Its ancestry includes *Hibiscus moscheutos* and *Hibiscus coccineus*. More specifically, the plant resulted from multiple crossings with an unnamed, Fleming *Hibiscus moscheutos* (nonpatented) and an unnamed Fleming *Hibiscus coccineus* (nonpatented). The seedling which most nearly met all of the above named standards was selected.

This new plant first bloomed in the summer of 1996 and was selected by David Fleming and Gretchen Zwetzig on David Fleming's property in Lincoln, Nebr. Asexual propagation of the plant by cuttings and root division has shown that the unique and distinguishing features of the plant are faithfully transmitted from generation to generation and appear to be fixed.

Since its origin, the plant has bloomed from midsummer until frost, while exhibiting the aforementioned distinctive characteristics. This Hardy Hibiscus plant greatly contributes to the market with its , sheer beauty and utter refinement, its compact growth habit, its enhanced resistance to disease and insects, its stability through extremes in rain and drought, and its extreme hardiness.

BRIEF DESCRIPTION OF THE DRAWINGS

The flower and foliage of the cultivar are shown in the attached photographs. More specifically the photograph is a semi close-up of the flower and the leaf.

The colors are as true as is reasonably possible to attain in photographic illustrations of this type. The colors illustrated may be slightly off due to light reflectance.

DESCRIPTION OF THE NEW PLANT

What follows is a detailed description of the new cultivar. The specific color descriptions are in accordance with The R.H.S Colour Chart, while general color recitations are consistent with ordinary American color terminology.

'Eruption' has not been observed under all possible environment conditions. It is to be understood that the phenotype may vary significantly with variations in environment such as temperature, light intensity, and day length, without, however any difference in genotype of the plant. The following botanical characteristics and observations are gathered from the plant when grown in Lincoln, Nebr. (USDA Zone 4).

THE PLANT

Parentage:
*Seed parent.—Hibiscus moscheutos,* Unnamed and unpatented Fleming seedling.
*Pollen parent.—Hibiscus coccineus* Unnamed and unpatented Fleming seedling.
Origin: A selected seedling from stated cross.
Type of plant: Hardy, herbaceous perennial
Classification: Variety of Hardy Hibiscus plant.
Propagation: Relatively easy to propagate; holds its distinguishing characteristics through successive cuttings and division.
Size: About 3–3½ feet tall and about 2½ ft. wide.

Form: Symmetrical annual growth from perennial roots.
Habit: Upright and uniformly branched.
Growth: Vigorous; medium and compact. Full grown (3–3½ ft.) in 2 years.
Hardiness: Hardy to at least −30 degrees Fahrenheit.
General health: Plant is very disease resistant against rot, aphids, spider mites, scale, white fly, etc.; sturdy through excessive drought, rain, or wind.
Propagation: Relatively easy and fast rooting in approximately 2 weeks.
Foliage:
1. *Arrangement.*—Alternate.
2. *Shape.*—Juvenile: 3–5 lobed "Maple to Oak-shaped" leaves. Rounded base shape. Mature: Refined, "Maple or Oak-shaped", 3–5 lobed leaf with entire to mildly serrate margins and acute apices; rounded base.
3. *Size.*—Mature leaf (petiole base to apex): Length is about 6 inches or 16 cm, width is about 10 inches or 25.5 cm.
4. *Color.*—Young leaves (upper side): 189-A, (purple cast) N 187-A. Mature leaves: (upper side): 189-A, (purple cast) N 187-A. Veins: 61-A. Coloration of the lower leaf surface: Closest to 191-A.
5. *Surface texture.*—Low sheen.
6. *Petiole length.*—About 2¾ inches or 6.5 cm.
7. *Petiole color.*—191-A.

Stems: The stems are stout at the base, becoming more slender toward the apices; coloration is consistent with the petiole.

THE FLOWER

Blooming period: Profuse from July until frost.
Flower diameter: Medium; about 9–10 inches (24 cm).
Borne: Singly in leaf axils, from midpoint of stems upward.
Bloom duration: Individual bloom lasts at least one full day.
Form: Campanulate; petals are also very overlapping.
Bud:
1. *Length.*—About 2½ inches (or 6 cm) on day before opening.
2. *Color.*—60-A.
3. *Surface texture.*—Semi-glabrous.
4. *Duration.*—One to two weeks.

Corolla: Having 5 petals.
1. *Petal character and dimensions.*—Campanulate and very overlapping. Length is about 5 inches or 12.5 cm. Width is about 5 inches or 12.5 cm.
2. *Coloration.*—Bright reddish-purple. (a) Reddish-purple petals: 61-B. Coloration of lower petal surface: 77-B and 61-B . (b) Veination in petals: 61-A. (c) Eye Zone: 53-A.
3. *Texture.*—Smooth.
4. *Substance.*—Thick.
5. *Shape.*—Campanulate and very overlapping.

Reproductive organs:
1. *Staminal column.*—Stamen along basal two-thirds. Stamen length: About 1¾ inches (or 4.8 cm). Stamen color: 67-A, and 69-B. Pollen color: 8-B.
2. *Style.*—Terminates upper one-third of staminal coumn. Stigmatic lobe color: Somewhere between 60-A and 60-B.

Calyx: Connate at the base; about 3¾ inches (or 9.5 cm) in length. Color: Medium green.
Stipules: None.
Epicalyx: Whorl of bracts.
1. *Shape.*—10 to 12 slender, sword-shaped bractlets.
2. *Length.*—About 1¼ inches (or 4.8 cm).
3. *Color.*—143-A.

Penduncle:
1. *Length.*—About 1½ inches (or 4 cm).
2. *Strength.*—Stiff and sturdy.
3. *Color.*—Light to medium green with slight reddish-purple cast.

GENERAL OBSERVATIONS

This plant, as a hybridized Hardy Hibiscus, is valuable to the landscape market for its improvements in thicker textured and brightly colored flowers and buds, refined, "Maple-like" or "Oak-like" green foliage with a purple cast, its all-around vigor, good breaking action, and adaptation to extreme environments, including the ability to consistently survive winter temperatures of at least −30 degrees Fahrenheit.

It is claimed:

1. A new and distinct cultivar of Hardy Hibiscus plant, as herein shown and described.

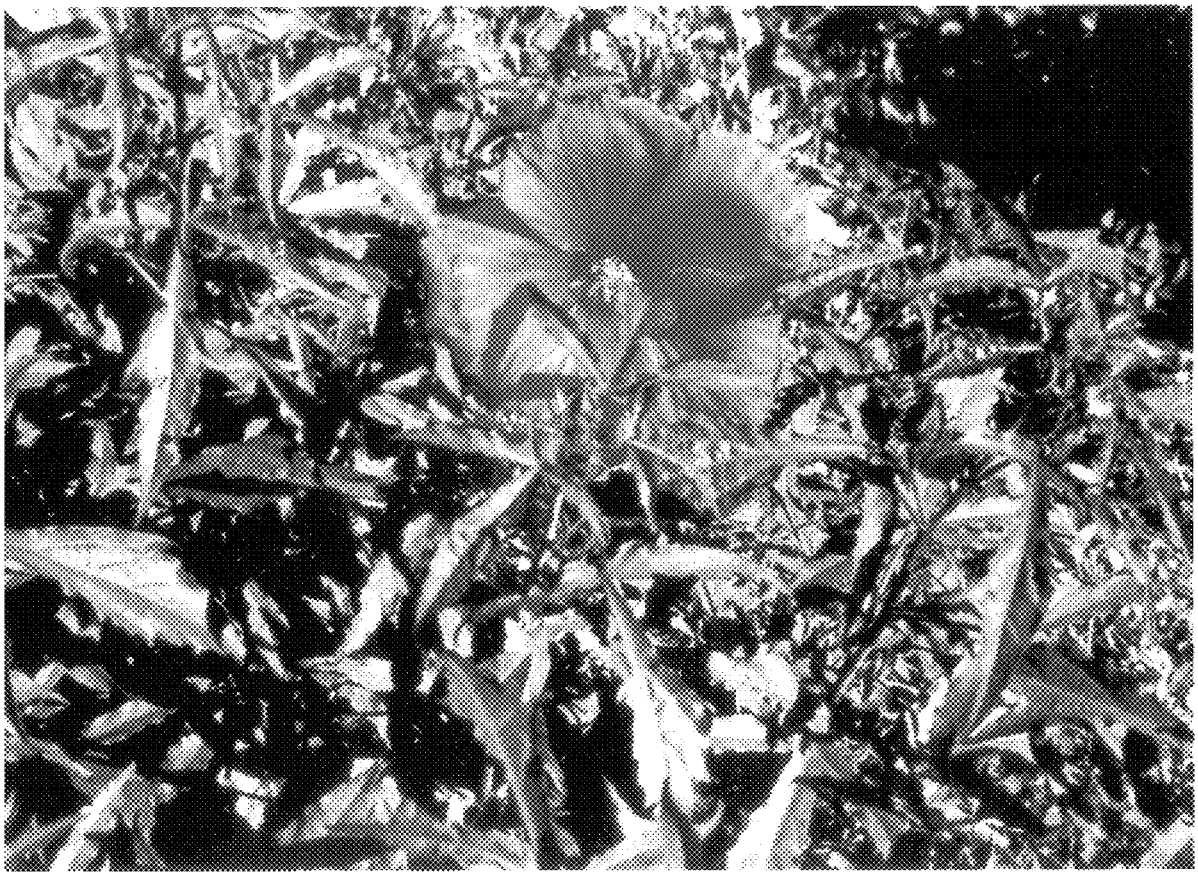

* * * * *